United States Patent [19]

Bickford

[11] 3,995,496

[45] Dec. 7, 1976

[54] DISPOSABLE MOUTH GUARD FOR PIPETTES

[76] Inventor: Albert G. Bickford, 2208 Humboldt Ave. South, Minneapolis, Minn. 55404

[22] Filed: Sept. 2, 1975

[21] Appl. No.: 609,349

[52] U.S. Cl. .............................. 73/425.6; 137/199
[51] Int. Cl.$^2$ ...................... B01L 3/02; G01N 1/14
[58] Field of Search .............. 137/199; 73/425.4 P, 73/425.6

[56] References Cited

UNITED STATES PATENTS

| | | | |
|---|---|---|---|
| 2,172,575 | 9/1939 | Caulfield | 73/425.6 |
| 2,410,552 | 11/1946 | Rosen | 73/425.6 |
| 3,166,940 | 1/1965 | Allisbaugh | 73/425.4 P |
| 3,290,946 | 12/1966 | Pursell | 73/425.6 |
| 3,732,734 | 5/1973 | Avakian | 73/425.6 |
| 3,748,909 | 7/1973 | Kuo | 73/425.4 P |

*Primary Examiner*—Alan Cohan
*Attorney, Agent, or Firm*—Stuart R. Peterson

[57] ABSTRACT

The disposable mouth guard prevents the flow of liquid into the user's mouth. It comprises a tubular sleeve of polyethylene formed with a trio of internal flexible or resilient ribs having an annular configuration disposed nearer one end of the sleeve, the first of the three ribs being inset from said one end of the sleeve so that the sleeve can be readily slipped over the suction end of a pipette. The innermost rib is spaced from an internal annular flange that functions as a stop for the end of the pipette. The annular flange also functions as one apertured wall of a chamber containing a fibrous material, more specifically cotton, which expands when liquid is drawn into the chamber, thereby preventing any of the liquid from entering the person's mouth. A second annular flange at the other end of the chamber confines the cotton in a recessed manner from the upper end of the mouth guard. Still another annular flange is formed at the upper end of the sleeve, this being concaved inwardly in order to conform to the user's finger to retain the liquid in the pipette.

13 Claims, 3 Drawing Figures

DISPOSABLE MOUTH GUARD FOR PIPETTES

BACKGROUND OF THE INVENTION

1. Field of the Invention

This invention relates generally to a disposable mouth guard that can be readily attached to the upper suction end of a pipette so as to prevent the drawing of liquid into the person's mouth.

2. Description of the Prior Art

In using a pipette, the usual procedure is for a person to suck at the upper end of the pipette to draw liquid into the pipette. In this way, various liquids can be readily measured or transferred. The difficulty stems from the fact that if too much liquid is drawn into the pipette it flows upwardly into the user's mouth. In many laboratories, noxious substances are handled and contact with the technician's mouth must be avoided, usually for the technician's safety but in any event to make even the pipetting of harmless liquids more appealing from a psychological standpoint. Instances where actual contact with the liquid is to be avoided for health reasons would include the handling of acids and bases. The technician would not wish to draw a portion of a blood sample or urine specimen into his mouth. Dyes used for staining slides are additional examples falling into the objectionable category.

The problem has been known for a long time, and various attempts have been made to solve the problem. In one instance, a system of check valves has been incorporated into the pipette itself. Also, attachments have made use of check valves. Fibrous materials have been utilized in various ways. However, all of the devices, whether embodied in the pipette itself or in an attachment therefor, have not met with any degree of commercial success, largely because they are too expensive in the first place, or at least are not sufficiently inexpensive such that they can be discarded after a single use. If not disposed of after having been used, any reuse demands that the attachment be resterilized each time, which has proved bothersome and costly.

SUMMARY OF THE INVENTION

Therefore, a primary object of my invention is to provide a mouth guard for pipettes that will be sufficiently inexpensive such that it can be discarded after a single use. In this regard, it is an aim of the invention to provide an attachment for preventing the drawing of liquid into a person's mouth from the pipette to which it is attached which attachment can be easily manufactured, readily sterilized at the factory, and packaged in such a way that it will remain sterilized until used.

Another object of the invention is to provide a mouth guard for pipettes which can be quickly placed over the upper or suction end of the pipette and which will remain firmly attached until deliberately removed. More specifically, no lubricants need be employed in effecting the attachment, and yet there will be the assurance that a sufficient retention will exist such that the mouth guard will remain in place on the pipette.

Another object is to provide a reliable sealing relationship between the mouth guard and the pipette so that no loss of vacuum results during the sucking of the liquid into the pipette and also during the period thereafter in which the liquid is held, usually by a person's finger placed over the upper end of the guard. In this latter respect, the invention has for a feature the provision of a concave upper end which conforms to the shape of the user's finger so that when his finger is placed directly on the upper end of the pipette the liquid will be effectively retained as long as desired.

Still another object of the invention is to provide an attachment for pipettes enabling a high degree of quality control to be adhered to. In this regard, a fibrous medium is contemplated which expands when contacted by the liquid after it has risen beyond the upper end of the pipette. It is important that the correct amount of fibrous material be contained in the mouth guard attachment so that requisite expansion takes place almost immediately, yet not have the material be so compacted that too much interference exists to the normal passage of air during the induction procedure. Consequently, an aim of the present invention is to permit just the right amount of fibrous material to be inserted within the mouth guard after the proper amount of such material has been experimentally ascertained. Stated somewhat differently, a chamber of predetermined size is provided so that when the correct amount of fibrous material is forced into the chamber it will be held under the proper compression so that when contacted by liquid it will become effective immediately to obstruct the flow. Also, an aim of the invention is to permit the insertion of the proper amount of fibrous material into the chamber, doing so without having to remove any portion of the sleeve, thereby allowing the guard to be fabricated in one piece.

Briefly, my invention contemplates the molding of a plastic sleeve, preferably of plasticized polyethylene, so that it can be readily slipped over the upper end of any conventional pipette. Provision is made for resiliently retaining the mouth guard in place on the pipette so that it will not inadvertently come off, and at the same time provide an effective seal so as not to interfere either with the filling of the pipette or the retention of the liquid in the pipette after it has been filled. Flexible or resilient ribs or rings are integral with the sleeve and extend sufficiently inward so as to releasably grip the upper end of the pipette when the mouth guard is placed thereon. The various ribs are quite thin so that they can be readily flexed.

Considerably thicker than the ribs is an annular flange which performs two functions: (1) it serves as a stop for the upper end of the pipette, and (2) it serves as one wall for the chamber in which the fibrous blocking material is contained. A second annular flange provides the other end wall for the chamber. Still a third annular flange, this being located at the upper end of the mouth guard, not only assures that there will be absolutely no contact between the person's tongue or any portion of his mouth and the fibrous medium, but at the same time permits the user to place his finger conveniently over the mouth guard to prevent the loss of liquid from the pipette after it has been filled.

It is planned that the mouth guard, when fabricated in accordance with my invention, be easily placed over any conventional pipette and equally easily withdrawn after it has served its purpose. Owing to the simplified construction, the mouth guard can be inexpensively manufactured, sufficiently so that it can be disposed of after but a single use.

BIREF DESCRIPTION OF THE DRAWING

DESCRIPTION OF THE PREFERRED EMBODIMENT

Figure 1:
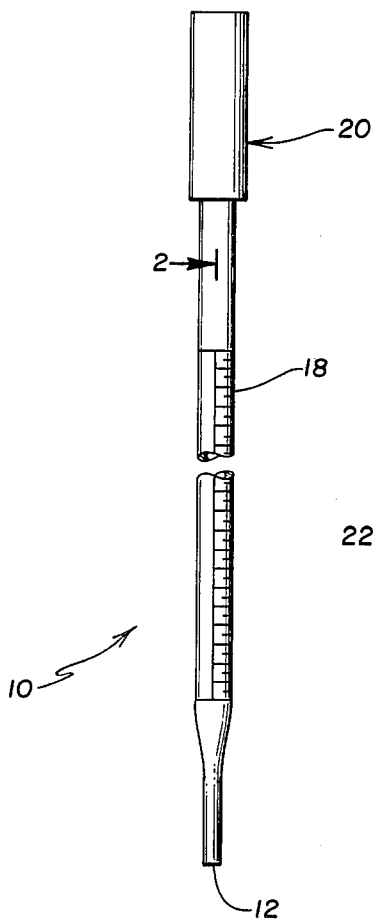
FIG. 1 is an elevational view of a conventional pipette with my mouth guard placed thereon.

A typical pipette has been illustrated in FIG. 1, being denoted generally by the reference numeral 10. The pipette 10 has an inlet 12 through which the liquid to be measured or transferred is drawn into the interior 16 of the pipette 10. Graduations 18 enable the user to determine how much liquid has been drawn into the pipette.

Figure 3:
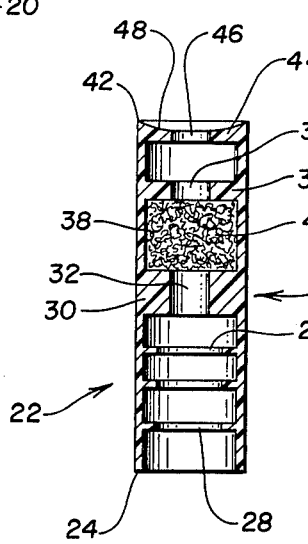
FIG. 3 is a sectional view corresponding to FIG. 2 but illustrating my mouth guard prior to the insertion of the pipette therein.

My mouth guard has been indicated generally by the reference numeral 20. It includes a sleeve 22 having a lower end 24 and three inwardly directed resilient ribs of annular configuration, each rib 26 forming an opening 28. It will be noted that the lowermost rib 26, as viewed in FIG. 3, is spaced upwardly or inset from the lower end 24. The several ribs 26 are spaced from each other so that each can be flexed by the pipette 10 without interference from each other.

Spaced above the uppermost rib 26 is an annular flange 30 having a centrally disposed hole 32 extending therethrough. It will be appreciated that the thickness of the flange 30 is considerably greater than the thickness of the rather thin ribs 26. The annular flange 30 functions as a stop for the upper end 14 of the pipette 10. Spaced upwardly from the annular flange 30 is a second annular flange 34 having a hole 36 exending therethrough. In this way, a chamber 38 is provided between the flanges 30 and 34 for the accommodation of fibrous material 40, preferably cotton that is held within the chamber by reason of the upper flange 34.

Located at the upper end 42 of the sleeve 22 is still another or third annular flange 44 having a central hole 46 extending therethrough. It will be seen that the upper face of the flange 44 is concave as denoted by the reference numeral 48. The purpose of the concave surface 48 is to enable a person to place one of his fingers over the opening 46 and thus keep any liquid that has been drawn into the interior 16 of the pipette 10 from being discharged via the inlet 12 until the discharge is desired.

Figure 2:
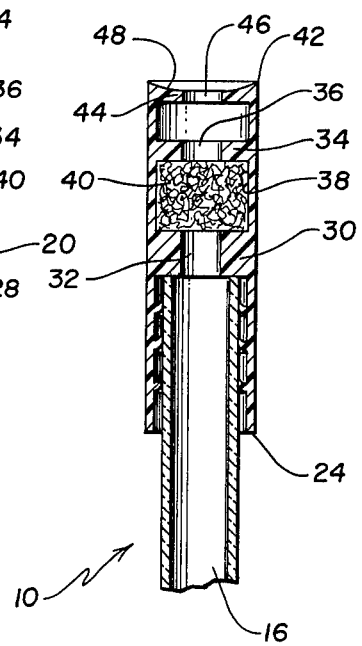
FIG. 2 is an enlarged sectional view taken in the direction of line 2—2 of FIG. 3.

The plastic comprising my mouth guard 20 should be somewhat flexible and resilient. It is preferred that it be of polyethylene having the necessary amount of plasticizer therein so as to make the entire sleeve 22 sufficiently flexible for its intended purpose. The specific amount of plasticizer will depend on the thickness of the sleeve 22, and more particularly on the thickness of the several ribs 26. The sleeve 22 itself should be relatively thin and more importantly yet the various ribs 26 therein should be thin enough (and contain enough plasticizer) so that they will flex upwardly when the pipette 10 is inserted. Polyethylene, it can be explained, has a natural waxiness to it so that it readily slips over the upper end of the pipette 10, the ribs 26 flexing into the condition depicted in FIG. 2 during the relative movement between the pipette 10 and mouth guard 20.

Much thicker is the annular flange 30 than the various ribs 26. Thus, the user is immediately apprised of when the full telescoping or mating of the pipette 10 and mouth guard 20 has been effected.

After placing the mouth guard 20 over the pipette 10, then the user inserts the upper end of the mouth guard 20 into his mouth and merely sucks as he would do when using a pipette without the mouth guard. This induces the liquid to enter through the inlet 12 to fill, or partially fill, the interior 16. Should the liquid be drawn upwardly through the hole 32 in the flange 30, it would enter into the chamber 38 and contact the cotton 40. The cotton 40 immediately expands so as to obstruct or block any further upward flow so that liquid cannot pass through the hole 36 in the flange 34. Added assurance is provided that no part of the person's mouth will even come close to the material 40 because the flange 34 is spaced beneath the topmost flange 44.

Although not illustrated, it is believed obvious that the concave surface 48 permits the user to close the opening 46 to prevent any air from entering which would release the confined liquid in the interior 16 of the pipette. However, when the liquid is to be discharged, then removal of one's finger from the opening 46 will permit the free downward flow of the liquid from the pipette 10.

It will be appreciated that the ribs 26 not only provide the requisite amount of yieldable or releasable retention as far as keeping the mouth guard 20 in place on the pipette 10, but they also provide an adequate seal so that during the sucking procedure air will not be drawn between the lower end 24 and the innerjacent portion of the pipette 10. The flexed ribs 26, as is believed obvious from FIG. 2, prevent any upward passage of air, the several ribs 26 acting as seals. Consequently, the suction created by the user is fully effective for drawing liquid into the pipette 10, there being no opportunity for air leakage in any parallel path. Even more importantly, though, is the sealing action that persists during the continued use of the pipette 10, particularly when the liquid contained therein is to be held until its intended release. The mere placing of a person's finger, although not depicted, over the hole 46 assures that there can be no air entering through the upper end of my mouth guard 20 and with air prevented from entering through the lower end 24 of the mouth guard 20, the liquid contained in the interior 16 of the pipette 10 is reliably retained.

The fibrous medium 40 is to be inserted at the factory. Assuming that cotton will be employed, the proper amount of cotton for the size of the chamber 38 can be determined, resorting to a trial and error technique if desired. Once ascertained, though, it will be appreciated that the same amount of cotton 40 can be forced downwardly through the hole 46, the upper flange 44 yielding sufficiently to permit this, and also downwardly through the hole 36 in the intermediate flange 34, the intermediate flange 34 also yielding sufficiently to permit the cotton 40 to pass through its hole 36. A simple rod or ram will accomplish this. Once the proper quantity of cotton 40 has been placed in the chamber 38, it is held captive by the flange 34. If the flange 34 were not used, then the cotton 40 would not be held under the requisite degree of compression so that it would expand sufficiently and rapidly enough when contacted by only a small amount of liquid. However, the compression of the cotton 40 is not so great as to interfere with the free passage of air which is needed to draw liquid into the pipette 10 by the user. The mouth guard 20 (with the exception of the cotton 40) is truly of unitary construction.

It is important that the cost of manufacturing my mouth guard 20 be as low as possible so that it can be employed for a single application and then discarded. Consequently, when handling various biological substances, there is no need to resterilize the mouth guard 20. All that need be done is to assure that the mouth guard 20 is initially packaged under sanitary and sterile conditions. Thus, laboratory personnel are relieved of the task of resterilizing my mouth guard, as they have had to do in the past, and at the same time the laboratory does not have to spend any large sums for the protection and convenience afforded by my invention.

I claim:

1. A one-piece disposable mouth guard for attachment to pipettes comprising a tubular sleeve having a plurality of internal flexible annular ribs near one end integral with said sleeve and extending from the inner surface of said sleeve, said sleeve having a chamber near the other end thereof, and a medium contained in said chamber for obstructing the flow of liquid therethrough.

2. A disposable mouth guard in accordance with claim 1 including a first internal annular flange located between the innermost of said ribs and said other end of said sleeve, said flange forming an apertured wall at one end of said chamber.

3. A disposable mouth guard in accordance with claim 2 including a second internal annular flange located between said first annular flange and said other end of said sleeve, said second annular flange forming a second apertured wall at the opposite end of said chamber from said one end thereof, said obstructing medium being confined between said flanges.

4. A disposable mouth guard in accordance with claim 3 in which said obstructing medium is cotton.

5. A disposable mouth guard in accordance with claim 3 including a third internal annular flange located at said other end of the sleeve, said second annular flange being spaced inwardly from said third annular flange.

6. A disposable mouth guard in accordance with claim 5 in which the outer surface of said third annular flange is concave.

7. A disposable mouth guard in accordance with claim 3 in which the rib nearest the said one end of said tubular sleeve is spaced inwardly from said one sleeve end.

8. A disposable mouth guard in accordance with claim 7 in which the thickness of said second annular flange is considerably greater than that of said ribs.

9. A disposable mouth guard in accordance with claim 8 in which the openings through said ribs are larger than the opening in said second annular flange.

10. A disposable mouth guard in accordance with claim 9 in which the material for said sleeve is plasticized polyethylene.

11. A disposable mouth guard in accordance with claim 3 in which said tubular sleeve has a cylindrical outer surface of uniform diameter.

12. A disposable mouth guard in accordance with claim 11 in which said inner surface is cylindrical and of a uniform diameter less than that of said outer surface.

13. A disposable mouth guard in accordance with claim 12 in which said ribs extend sufficiently from said inner cylindrical surface so as to be flexed toward said other end of the sleeve when said one end of said sleeve receives a pipette therein.

* * * * *